United States Patent [19]
El-Nokaly et al.

[11] Patent Number: 5,688,831
[45] Date of Patent: Nov. 18, 1997

[54] COSMETIC MAKE-UP COMPOSITIONS

[75] Inventors: Magda El-Nokaly, Cincinnati, Ohio; Kataline Igo-Kemenes, Thorpe Green, Great Britain; David Andrew Jakubovic; Anne Langlois, both of Staines, Great Britain; Michael Lee Vatter, Okeana, Ohio

[73] Assignee: The Procter & Gamble Company, Cincinnati, Ohio

[21] Appl. No.: 557,019

[22] PCT Filed: May 16, 1994

[86] PCT No.: PCT/US94/05439

§ 371 Date: Dec. 6, 1995

§ 102(e) Date: Dec. 6, 1995

[87] PCT Pub. No.: WO94/28860

PCT Pub. Date: Dec. 22, 1994

[30] Foreign Application Priority Data

Jun. 11, 1993 [GB] United Kingdom ............ 9312100

[51] Int. Cl.⁶ ............................. A01N 65/00
[52] U.S. Cl. ............ 514/938; 424/59; 424/69; 424/78.02; 424/78.03; 514/844; 514/845; 514/944
[58] Field of Search ............ 424/400, 401, 424/59, 69, 78.03, 78.02; 514/944, 938, 844, 845

[56] References Cited

U.S. PATENT DOCUMENTS

| | | | |
|---|---|---|---|
| 3,444,291 | 5/1969 | Bivans | 424/63 |
| 3,957,971 | 5/1976 | Oleniacz | 424/70 |
| 4,046,886 | 9/1977 | Smith | 424/227 |
| 4,486,405 | 12/1984 | Klein | 424/59 |
| 4,659,562 | 4/1987 | Arraudeau | 424/63 |
| 4,767,625 | 8/1988 | Mitsuno et al. | 424/94 |
| 4,804,532 | 2/1989 | Busch, Jr. | 424/69 |
| 4,999,348 | 3/1991 | Cioca et al. | 514/171 |
| 5,061,481 | 10/1991 | Suzuki et al. | 424/63 |
| 5,143,722 | 9/1992 | Hollenberg et al. | 424/63 |
| 5,215,757 | 6/1993 | El-Nokaly | 424/488 |
| 5,266,321 | 11/1993 | Shukuzaki et al. | 424/401 |
| 5,412,004 | 5/1995 | Tachibana et al. | 524/27 |

FOREIGN PATENT DOCUMENTS

| | | | |
|---|---|---|---|
| 0534823B1 | 3/1993 | European Pat. Off. | A61K 7/00 |
| 62-205187 | 9/1987 | Japan | A61K 7/00 |
| 62-205188 | 9/1987 | Japan | A61K 7/00 |
| 0 512270A2 | 11/1992 | Japan | A61K 7/48 |
| 3-111715 | 11/1992 | Japan | A61K 7/00 |
| WO94/06400 | 3/1994 | WIPO | A61K 7/00 |

OTHER PUBLICATIONS

Nakamura et al., "Blurring of Wrinkles Through Control of Optical Properties", *Preprints of the XIVth I.F.S.C.C. Congress, Barcelona*, vol. 1, pp. 51–63, 1986.

Cioca et al., "Liquid Crystals and Cosmetic Applications", *Cosmetics & Toiletries*, vol. 105, pp. 57–62, 1990.

Bevacqua et al., "Liquid Crystals in Multiple Emulsions", *Cosmetics & Toiletries*, vol. 106, pp. 53–66, 1991.

*Primary Examiner*—Terressa Mosley
*Attorney, Agent, or Firm*—John M. Howell; T. David Reed; David L. Suter

[57] ABSTRACT

A make-up composition in the form of a water-in-oil emulsion comprising a silicone phase, humectant, pigment and organic amphiphilic material capable of forming smectic lyotropic liquid crystals in product or on the skin. The make-up composition exhibits superior short and longer term moisturisation and skin feel, together with improved product stability and spreadability.

25 Claims, No Drawings

COSMETIC MAKE-UP COMPOSITIONS

FIELD OF THE INVENTION

The present invention relates to cosmetic make-up compositions and more particularly, to pigmented foundation make-up compositions and blushers having improved moisturisation effectiveness. The compositions incorporate an amphiphilic material which is capable of forming liquid crystals.

BACKGROUND OF THE INVENTION

A foundation composition can be applied to the face and other parts of the body to even skin tone and texture and to hide pores, imperfections, free lines and the like. A foundation composition is also applied to moisturize the skin, to balance the oil level of the skin and to provide protection against the adverse effects of sunlight, wind and the harsh environment.

Make-up compositions are generally available in the form of liquid or cream suspensions, emulsions, gels, pressed powders or anhydrous oil and wax compositions.

U.S. Pat. No. 3,444,291 discloses a method of filling and camouflaging skin cavities by applying a composition which includes 65 to 75 parts by weight of a microcrystalline wax and about 25 to 35 pans of a mineral oil. The composition includes a colourant, preferably a coal tar dye, for example, D & C Red No. 17, which matches the colour of the user's skin.

A spreadable, flowable and greaseless cosmetic cover-up composition is taught in U.S. Pat. No. 4,486,405. That composition is characterized by the presence of a first and a second alkoxylated surfactant present in substantially the same concentration.

U.S. Pat. No. 4,804,532 recites a facial cosmetic powder which utilizes crystalline silica in much lower concentration than that employed in the then prior art compositions. This powder, used as a blush or a facial coating, is said to be effective in hiding skin wrinkles, lines and pores. The composition is a mixture of a colour phase and a diluent phase. The colour phase is formed by blending crystalline silica with colourants. The resultant colour phase is mixed with the diluent phase, essentially formed from nacreous materials such as talc and mica, to form the composition.

The use of a foundation composition which has a significantly high concentration of naereous material is taught in U.S. Pat. No. 3,978,207. This foundation, a pressed powder composition, is characterized by the presence of a nacreous material such as mica and a binder oil which provides a frosted pearl effect, that is, a lustrous look. The colour of this foundation is provided by the nacreous material.

U.S. Pat. No. 4,659,562 discloses a cosmetic make-up composition which includes, as a binding agent therefore, an intimate mixture of from 5 to 95 weight percent of a mixture of finely divided silica and about 5 to 95 weight percent of finely divided polyethylene fibres. The composition is recited to maintain its uniformity over the areas of the skin to which it is applied. That is, it is said to be "creaseproof". The composition of the '562 patent includes colourant in admixture with nacreous agents.

Nakamura et al., Preprints of the XIVth I.F.S.C.C. Congress, Barcelona, 1986, Vol. I, 51–63 (1986) describes a novel make-up composition utilizing spherical silica and polydimethyl siloxane. This combination is recited to provide a foundation which reduces wrinkle visibility to a greater extent than make-up foundations with which it was compared. This reduction in wrinkle visibility is caused by optical blurring enhanced by the novel use of spherical silica and polydimethyl siloxane.

U.S. Pat. No. 5,143,722 discloses a cosmetic make-up composition comprising water-in-oil emulsions comprising pigment coated with polysiloxane, a silicone phase, a water phase and a polydiorganosiloxane-polyoxyalkylene copolymeric surfactant.

Foundations in the form of water-in-oil emulsions are well known and provide good coverage and good skin feel, wear and appearance. These have, however, not been successful from the viewpoint of moisturisation.

In the past, humectants such as water-soluble polyglycerylmethacrylate lubricants and glycerine have been incorporated into skin and hair gel compositions for use as moisturisation agents. These compositions have provided improvements in moisturisation, absorption, skin feel, residue and skin care characteristics compared with conventional cosmetic cream and lotion compositions. There is still a need, however, for enhanced moisturisation both in the short and longer term and also increased emulsion stability, skin feel and spreadability.

Liquid crystals are a special phase of matter. The liquid crystal phase exists between the boundaries of the solid phase and the isotropic liquid phase (i.e. an intermediate between the three dimensionally ordered crystalline state and the disordered dissolved state). In the liquid crystal state, some of the molecular order characteristics of the solid phase are retained in the liquid state because of molecular association structure and long range intermolecular order. The ability of some compounds to form a liquid crystalline mesophase had been observed nearly a century ago. Since that time many compounds exhibiting liquid crystalline properties have been synthesized and have been used to encapsulate and act as a delivery vehicle for drugs, flavours, nutrients and other compounds.

It is accordingly a primary object of this invention to provide a make-up composition in the form of a water-in-oil emulsion, particularly a water-in-silicone emulsion, comprising an amphiphilic material capable of forming liquid crystals.

It is also an object of the invention to provide a pigmented make-up composition in the form of a water-in-silicone emulsion which exhibits improved short and longer term moisturisation together with good product stability, good skin-feel and good spreadability.

It is a further object of the invention to provide emulsion-form make-up compositions containing humectants and which provide improved moisturisation effectiveness.

SUMMARY OF THE INVENTION

In accordance with one aspect of the present invention, there is provided a make-up composition in the form of a water-in-oil emulsion comprising:

a) from about 1% to about 50% by weight of silicone oil selected from volatile silicones, non-volatile silicones and mixtures thereof, b) from about 0.1% to about 30% by weight of humectant, c) from about 0.1% to about 25% by weight of pigment, and d) from about 0.1% to about 20% by weight of an organic amphiphilic material which is capable of forming smectic lyotropic liquid crystals in product or on the skin.

The water-in-oil emulsions of the present invention provide improved short and longer term moisturisation together with excellent skin feel, spreadability and product stability.

According to another aspect of the present invention there is provided a make-up composition in the form of a gel or emulsion comprising:

a) from about 0.1% to about 30% by weight of humectant, b) from about 0% to about 25% by weight of pigment, c) from about 0.1% to about 20% by weight of an organic amphiphilic material which is capable of forming smectic lyotropic liquid crystals in product or on the skin, and d) water.

All levels and ratios are by weight of total composition, unless otherwise indicated. Chain length and degrees of alkoxylation are also specified on a weight average basis.

DETAILED DESCRIPTION OF THE INVENTION

The make-up composition according to one aspect of the present invention comprises a mixture of volatile and/or non-volatile silicones, humectant, pigment and organic amphiphilic material capable of forming lyotropic liquid crystals in product or on the skin. The composition is in the form of a water-in-oil emulsion.

A first essential component of the water-in-oil emulsion is a silicone oil which in preferred embodiments comprises a mixture of volatile silicones and non-volatile silicones. The silicone oil is present in an amount of from about 1% to about 50% by weight. Suitable volatile silicone oils include cyclic and linear volatile polyorganosiloxanes (as used herein, "volatile" refers to those materials which have a measurable vapour pressure at ambient conditions).

A description of various volatile silicones is found in Todd, et al., "Volatile Silicone Fluids for Cosmetics", 91 *Cosmeacs and Toiletries* 27–32 (1976).

Preferred cyclic silicones include polydimethylsiloxanes containing from about 3 to about 9 silicon atoms, preferably containing from about 4 to about 5 silicon atoms. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 21330, Dow Corning 345, and Dow Corning 200 (manufactured by the Dow Corning Corporation): Silicone 7207 and Silicone 7158 (manufactured by the Union Carbide Corporation). SF:202 (manufactured by General Electric) and SWS-03314 (manufactured by Stauffer Chemical).

Suitable non-volatile silicones preferably have an average viscosity of from about 1,000 to about 2,000,000 mm$^2$.s$^{-1}$ at 25° C. more preferably from about 10,000 to about 1,800,000 mm$^2$.s$^{-1}$, even more preferably from about 100,000 to about 1,500,000 mm$^2$.s$^{-1}$. Lower viscosity non-volatile silicone conditioning agents, however, can also be used.

Viscosity can be measured by means of a glass capillary viscometer as set forth in Dow Corning Corporate Test Method CTM0004, Jul. 20, 1970. Suitable non-volatile silicone fluids for use herein include polyalkyl siloxanes, polyaryl siloxanes, polyalkylaryl siloxanes, polysiloxanes with amino functional substitutions, polyether siloxane copolymers, and mixtures thereof. The siloxanes useful in the present invention may be endcapped with any number of moieties, including, for example, methyl, hydroxyl, ethylene oxide, propylene oxide, amino and carboxyl. However, other silicone fluids having skin conditioning properties may be used. The non-volatile polyalkyl siloxane fluids that may be used include, for example, polydimethylsiloxanes. These siloxanes are available, for example, from the General Electric Company as a Viscasil (RTM) series and from Dow Corning as the Dow Corning 200 series. Preferably, the viscosity ranges from about 10 mm$^2$.s$^{-1}$ to about 100,000 mm$^2$.s$^{-1}$ at 25° C. The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used.

References disclosing suitable silicone fluids include U.S. Pat. No. 2,826,551, Green; U.S. Pat. No. 3,964,500, Drakoff, issued Jun. 22nd, 1976; U.S. Pat. No. 4,364,837, Pader; and GB-A-849,433, Woolston. In addition, Silicone Compounds distributed by Petrarch Systems Inc., 1984 provides an extensive (though not exclusive) listing of suitable silicone fluids.

Preferred non-volatile silicones for use herein include polydiorganosiloxane-polyoxyalkylene copolymers containing at least one polydiorganosiloxane segment and at least one polyoxyalkylene segment, said polydiorganosiloxane segment consisting essentially of

siloxane units wherein b has a value of from about 0 to about 3, inclusive, there being an average value of approximately 2 R radicals per silicon for all siloxane units in the copolymer, and R denotes a radical selected from methyl, ethyl, vinyl, phenyl and a divalent radical bonding said polyoxyalkylene segment to the polydiorganosiloxane segment, at least about 95% of all R radicals being methyl; and said polyoxyalkylene segment having an average molecular weight of at least about 1000 and consisting of from about 0 to about 50 tool percent polyoxypropylene units and from about 50 to about 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from about 2 to about 8. Such polymers are described in U.S. Pat. No. 4,268,499.

More preferred for use herein are polydiorganosiloxane-polyoxyalkylene copolymers having the general formula:

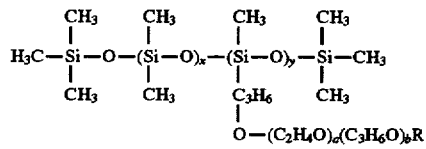

wherein x and y are selected such that the weight ratio of polydiorganosiloxane segments to polyoxalkylene segments is from about 2 to about 8, the mol ratio of a:(a+b) is from about 0.5 to about 1, and R is a chain terminating group, especially selected from hydrogen; hydroxyl; alkyl, such as methyl, ethyl, propyl, butyl, benzyl; aryl, such as phenyl; alkoxy such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino, such as dimethylamino.

The number of and average molecular weights of the segments in the copolymer are such that the weight ratio of polydiorganosiloxane segments to polyoxyalkylene segments in the copolymer is preferably from about 2.5 to about 4.0.

Suitable copolymers are available commercially under the tradenames Belsil CRTM) from Wacker-Chemie GmbH, Geschaftsbereich S, Postfach D-S8000 Munich 22 and Abil (RTM) from Th. Goldschmidt Ltd,. Tego House, Victoria Road, Ruislip, Middlesex, HA4 OYL. Particularly preferred for use herein are Belsil (RTM) 6031, Abil (RTM) B88183 and DC3225C. A preferred silicone herein is known by its CTFA designation as dimethicone copolyol.

The silicone oil phase preferably comprises from about 2% to about 25%, more preferably from about 5% to about 15% by weight of composition of non-volatile silicones.

An essential component of the compositions herein is a humectant or mixture of humectants. The humectant or mixture of humectants herein is present in an amount of from about 0.1% to about 30% preferably from about 5% to about 25%, and more preferably from about 10% to about 20% by weight of composition. Suitable humectants are selected from glycerine and polyglycerylmethacrylate lubricant having a viscosity at 25° C. of 300,000 to 1,100,000 cps; a specific gravity at 25° C. of 1 to 1.2g/ml, a pH of 5.0 to 5.5; a bound water content of 33 to 58%; and, a free water content from 5 to 20%.

In preferred embodiments, the humectant is incorporated at least partly into the oil phase of the water-in-oil emulsion so as to form a multiphase humectant-in-oil-in-water dispersion. The oil phase preferably comprises from about 0.1% to about 10%, more preferably from about 0.1% to about 3% by weight of humectant on a composition basis. Suitably, the humectant is introduced into the oil phase in the form of a mixture with or incorporated within a particulate lipophilic or hydrophobic carrier material. Humectant can also be introduced via the liquid crystal internal solvent phase.

Polyglycerylmethacrylate lubricants having the desired properties are marketed by Guardian Chemical Corporation under the trademark "Lubrajel". The "Lubrajels" identified as "Lubrajel DV", "Lubrajel MS", and "Lubrajel CG" are preferred in the present invention. The gelling agents sold under these trademarks contain about 1% propylene glycol.

Other suitable humectants include sorbitol, panthenols, propylene glycol, butylene glycol, hexylene glycol, alkoxylated glucose derivatives, such as Glucam (RTM) E-20, hexanetriol, and glucose ethers, and mixtures thereof. Urea is also suitably added as a humectant in the internal aqueous phase.

The panthenol moisturiser can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex.

The preferred humectant herein is glycerine. Chemically, glycerine is 1,2,3-propanetriol and is a product of commerce.

A further essential component of the compositions herein is an organic amphiphilic material which is capable of forming smectic lyotropic crystals in product or when the product is applied on the skin at ambient or elevated temperatures. Preferably the amphiphilic material is capable of forming smectic lyotropic liquid crystals at a temperature in the range from about 20° C. to about 40° C. The amphiphilic material is present at a level of from about 0.1% to about 20%, preferably from about 0.1% to about 10%, by weight.

The liquid-crystal forming amphiphilic materials suitable for use herein contain both hydrophilic and lipophilic groupings and exhibit a marked tendency to adsorb at a surface or interface, i.e. they are surface-active. Surface-active materials are divided into nonionic (no charge), anionic (negative charge), cationic (positive charge) and amphoteric (both charges) based on whether or not they ionize in aqueous media.

In the literature, liquid crystals are also referred to as anisotropic fluids, a fourth state of matter, surfactant association structure or mesophases. Those terms are often used interchangeably. The term "liquid crystals" as used herein means "smectic lyotropic liquid crystals" unless otherwise specified. The term "lyotropic" means a liquid crystalline system containing a polar solvent. In preferred embodiments herein the polar solvent is water or a solution of humectant in water. Smectic lyotropic liquid crystals are to be distinguished from thermotropic, heat; magnetically induced or cholesteric liquid crystals. The liquid crystals used herein are preferably lamellar, hexagonal, rod or vesicle structures or mixtures thereof. The amphiphilic material/polar solvent is substantially one phase—i.e. at least 90% is in the form of the liquid crystal.

The liquid crystalline phase utilized in the compositions of the invention can be identified in various ways. A liquid crystal phase flows under shear and is characterised by a viscosity that is significantly different from the viscosity of its isotropic solution phase. Rigid gels do not flow under shear like liquid crystals. Also, when viewed with a polarized light microscope, liquid crystals show identifiable birefringence, as, for example, planar lamellar birefringence, whereas when isotropic solutions and rigid gels are viewed under polarized light, both show dark fields.

Other suitable means for identifying liquid crystals include X-ray diffraction, NMR spectroscopy and transmission electron microscopy.

In general terms, the organic amphiphilic material preferred for use herein can be described as a liquid, semi-solid or waxy water-dispersible material having the formula X-Y where X represents a hydrophilic, especially nonionic moiety and Y represents a lipophilic moiety.

Organic amphiphilic materials suitable for use herein include those having a weight average HLB (Hydrophilic Lipophilic Balance) in the range from about 2 to about 12, preferably from about 4 to about 8.

Preferred organic amphiphilic materials employed herein have a long saturated or unsaturated branched or linear lipophilic chain having from about 12 to about 30 carbon atoms such as oleic, lanolic, tetradecylic, hexadecylic, isostearylic, laurie or alkyl phenyl chains. When the hydrophilic group of the amphiphilic material forming the liquid crystal phase is a nonionic group, a polyoxyethylene, a polyglycerol, a polyol ester, oxyalkylated or not, and, for example, a polyoxyalkylated sorbitol or sugar ester, can be employed. When the hydrophilic group of the amphiphilic material forming the liquid crystal phase is an ionic group, advantageously there can be used, as the hydrophilic group, a phosphatidylcholine residue as found in lecithin.

Nonionic amphiphilic components preferred for use herein are selected from:

(1) ethers of linear, or branched, polyglycerol having the following formula:

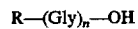

wherein n is a whole number between 1 and 6, R is selected from aliphatic, linear or branched, saturated or unsaturated chains of 12 to 30 carbon atoms, the hydrocarbon radicals of lanolin alcohols and the 2-hydroxy alkyl residue of long chain, alpha-diols, and Gly represents a glycerol residue;

(2) polyethoxylated fatty alcohols, for example those of the formula $R^1(C_2 R_4O)_x$ OH wherein $R_1$ is $C_{12}$–$C_{30}$ linear or branched alkyl or alkenyl and x averages from about 0 to about 20, preferably from about 0.1 to about 6, more preferably from about 1 to about 4;

(3) polyol esters and polyalkoxylated polyol esters, and mixtures thereof, the polyols preferably being selected from sugars, $C_2$–$C_6$ alkylene glycols, glycerol, polyglycerols, sorbitol, sorbitan, polyethylene glycols and polypropylene glycols and wherein the polyalkoxylated polyol esters contain from about 2 to about 20 preferably from about 2 to about 4 moles of alkylene oxide (especially ethylene oxide) per mole of polyol ester;

(4) natural and synthetic phosphoglycerides, glycolipids and sphingolipids, for example cerebrosides, ceramides and lecithin.

Examples of other organic amphiphilic materials suitable for use herein include $C_8$–$C_{30}$ alkyl and acyl-containing amphoteric, anionic, cationic and nonionic surfactants as set out below.

Amphoteric

N-alkyl amino acids (e.g., sodium N-alkylaminoacetate); N-lauroylglutamic acid cholesterol ester (e.g., Eldew CL-301 Ajinomoto)

Anionic

Acylglutamates (e.g., disodium N-lauroylglutamate);

Sarcosinates (e.g., sodium lauryl sarcosinate. Grace, Seppic);

Taurates (e.g., sodium lauryl taurate. sodium methyl cocoyl taurate);

Carboxylic acids and salts (e.g., potassium oleate; potassium laurate;

potassium-10-undecenoate; potassium 11-(p-styryl)—undecanoate);

Ethoxylated carboxylic salts (e.g., sodium carboxy methyl alkyl ethoxylate);

Ether carboxylic acids;

Phosphoric acid esters and salts (e.g., lecithin; DEA-oleth-10 phosphate);

Acyl isethionates (e.g., sodium 2-1auroyloxyethane sulfonate);

Alkane sulfonates (e.g., branched sodium x-alkane sulfonate (x/1);

Sulfosuccinates e.g.,

Sodium dibutyl sulfosuccinate,

Sodium di-2-pentyl sulfosuccinate,

Sodium di-2-ethylbutyl sulfosuccinate,

Sodium di-hexyl-sulfosuccinate,

Sodium di-2 ethylhexyl sulfosuccinate (AOT),

Sodium di-2-ethyldodecyl sulfosuccinate,

Sodium di-2-ethyldodecyl sulfosuccinate,

Dioctyl sodium sulfosuccinate,

Disodium laureth sulfosuccinate (MacKanate El, Mcintyre Group Ltd.)

Sulfuric acid esters (e.g., sodium 2-ethylhept-6-enyl sulfate; sodium 11-heneicosyl sulfate; sodium 9-heptadecyl sulfate).

Alkyl sulfates (e.g., MEA alkyl sulfate such as MEA-lauryl sulfate)

Cationic

Alkyl Imidazolines (e.g., alkyl hydroxyethyl imidazoline, stearyl hydroxyethyl imidazoline (supplier Akzo, Finetex and Hoechst));

Ethoxylated Amines (e.g., PEG-n alkylamine, PEG-n alkylamino propylamine, Poloxamine, PEG-coeopolyamine, PEG- 15 tallow amine);

Alkylamines (e.g., dimethyl alkylamine; dihydroxyethyl alkylamine dioleate)

Quaternaries:

Alkylbenzyl dimethylammonium salts (e.g., stearalkonium chloride);

Alkyl betaines (e.g., dodecyl dimethyl ammonio acetate, oleyl betaine);

Heterocyclic ammonium salts (e.g., alkylethyl morpholinium ethosulfate);

Tetraalkylammonium salts (e.g., dimethyl distearyl quaternary ammonium chloride (Witco));

Bis-isostearamidopropyl hydroxypropyl diammonium chloride (Schercoquat 21AP from Scher Chemicals);

1,8-Bis (decyldimethylammonio)-3, 6 dioxaoctane ditosylate

Nonionic Surfactants

Ethoxylated glycerides;

Monoglycerides (e.g., monoolein; monolinolein; monolaurin; 1-dodecanoyl-glycerol monolaurin; 1, 13-docosenoyl-glycerol monoerucin diglyceride fatty acid (e.g., diglycerol monoisostearate Cosmol 41, fractionated. Nisshin Oil Mills Ltd.);

Polyglyceryl esters (e.g., triglycerol monooleate (Grindsted TS-T122), diglycerol monooleate (Grindsted TST-T101);

Polyhydric alcohol esters and ethers (e.g., sucrose monooleate (Ryoto, Mitsubishi-Kasei Food Corporation), cetostearyl glucoside (Montanol, Seppic), β octyl glucofuranoside esters, alkyl glucoside such $C_{10}$–$C_{16}$ (Henkel));

Diesters of phosphoric acid (e.g., sodium dioleyl phosphate);

Alkylamido propyl betaine (e.g., cocoamido propyl betaine);

Amide: (e.g., N-(dodecanoylaminoethyl)-2-pyrrolidone);

Amide oxide: e.g., 1, 1 Dihydroperfluorooctyldimethylamine oxide,

Dodecyldimethylamine oxide,

2-Hydroxydodecyldimethylamine oxide,

2-Hydroxydodecyl-bis (2-hydroxyethyl) amine oxide,

2-Hydroxy-4-oxahexadecyldimethylamine oxide,

Ethoxylated amides (e.g., PEG-n acylamide);

Ammonio phosphates (e.g., didecanoyl lecithin);

Amine (e.g., octylamine);

Ammonio amides e.g.,

N-trimethylammoniodecanamidate,

N-trimethylammoniododecanamidate,

Ammonio carboxylates e.g., dodecyldimethylammonioacetate, 6-didodecylmethylammoniohexanoate, Phosphonic and phosphoric esters and amides e.g., methyl-N-methyl-dodecylphosphonamidate, dimethyl dodecylphosphonate, dodecyl methyl methylphosphonate, N,N-dimethyl dodeeylphosphonic diamide Ethoxylated alcohols Polyoxyethylene ($C_8$) e.g., pentaoxyethylene glycol p-n-octylphenyl ether hexaoxyethylene glycol p-n-octylphenyl ether
nonaoxyethylene glycol p-n-octylphenyl ether
Polyoxyethylene ($C_{10}$) e.g.,
pentaoxyethylene glycol p-n-decylphenyl ether,
decyl glyceryl ether, 4-oxatetradecan-1, 2-diol,
nonaoxyethylene glycol p-n-decylphenyl ether
Polyoxyethylene ($C_{11}$) e.g.,
Tetraoxyethylene glycol undecyl ether
Polyoxyethylene ($C_{12}$) e.g.,
3, 6, 9, 13-tetraoxapentacosan 1, 11-diol,
3, 6, 10-trioradocosan-1, 8-diol,
3, 6, 9, 12, 16-pentaoxaoctacosan 1, 14-diol,
3,6,9,12,15-pentaoxanonacosan-1, 17-diol,
3, 7-dioxanonadecan-1, 5-diol,
3, 6, 12, 15, 19-hexaoxahentriacontan-1, 16-diol,
pentaoxyethylene glycol dodecyl ether,
monoaxyethylene glycol p-n-dodecylphenyl ether,
Polyoxyethylene($C_{14}$) e.g.,
3, 6, 9, 12, 16-pentaoxaoctacosan-1, 14-diol,
3, 6, 9, 12,15,19-hexaoxahentriacontan-1, 17-diol,
Sulfone diimines e.g.,
decyl methyl sulfone diimine
Sulfoxides e.g.,
3-decyloxy-2-hydroxypropyl methyl sulfoxide
4-decyloxy-3-hydroxybutyl methyl sulfoxide
Sulfoximines e.g.,
N-methyl dodecyl methyl sulfoximine Highly preferred organic amphiphilic materials for use herein are selected from sugar esters and polyalkoxylated sugar esters and phophatides such as lecithin.

The sugar esters for use in this invention can be classified as hydrocarbyl and alkyl polyoxyalkylene esters of cyclic polyhydroxy saccharides wherein one or more of the hydroxyl groups on the saccharide moiety is substituted with an acyl or polyoxyalkylene group. Hydrocarbyl sugar esters can be prepared in well-known fashion by heating an acid or acid halide with sugar, i.e., by a simple esterification reaction.

The sugars employed in the preparation of the sugar esters include monosaccharides, di-saccharides and oligosaccharides well known in the art, for example, the dextrorotatory and levorotatory forms of glucose, fructose, mannose, galactose, arabinose and xylose. Typical di-saccharides include maltose, cellibiose, lactose, and trehalose. Typical tri-saccharides include raffinose and gentianose. The di-saccharides are preferred for use herein, especially sucrose.

Sucrose can be esterified at one or more of its eight hydroxyl groups to provide the sucrose esters useful herein. When sucrose is combined with an esterification agent in a 1:1 mole ratio, sucrose monoesters are formed; when the ratio of esterification agent to sucrose is 2: 1, or greater, the di-, tri-, etc., esters are formed, up to a maximum of the octa-ester.

Preferred sugar esters herein are those prepared by the esterification of sugars at a mole ratio of esterification agent:sugar of 1:1 and 3:1 i.e., the mono-acyl and di- or higher acyl sugar esters. Especially preferred are the mono-, di- and tri-acyl sugar esters and mixtures thereof wherein the acyl substituents contain from about 8 to about 20 carbon atoms and 0, 1 or 2 unsaturated moieties. Of the mono-acyl and di-acyl sugar esters, the respective esters of di-saccharide sugars, especially sucrose, wherein the acyl groups contain from about 8 to about 20 carbon atoms are especially preferred. Preferred sugar esters herein are sucrose monooctanoate, sucrose monodecanoate, sucrose monolaurate, sucrose monomyristate, sucrose monopalmitate, sucrose monostearate, sucrose monooleate, sucrose monolinoleate, sucrose dioleate, sucrose dipalmitate, sucrose distearate, sucrose dilaurate and sucrose dilinoleate, and mixtures thereof. Sucrose oleates and palmitates have been found to be particularly efficacious in the compositions herein. In mixtures of mono-acyl with di-, tri- and higher acyl sugar esters, the mono-- and di-acyl esters preferably comprise at least about 40%, more preferably from about 50% to about 95% by weight of the total sugar ester mixture.

Other sugar esters suitable for use in the compositions of this invention are the alkyl polyoxyalkylene sugar esters wherein one hydroxyl group is substituted with a $C_8$–$C_{18}$ alkyl group and wherein one or more of the hydroxyl groups on the sugar molecule are replaced by an ester or ether substituent containing the moiety $[(CH_2)_x\text{—}O]_y$, wherein x is an integer from 2 to about 4, preferably 2, and wherein y is an integer from about 1 to about 50, preferably 8 to 30 polyoxyalkylene substituents. Especially preferred herein are sugar esters wherein the polyoxyalkylene substituent is a polyoxyethylene substituent containing from about 8 to about 30 polyoxyethylene groups. Such materials wherein sorbitan is the sugar moiety are commercially available under the tradename "Tweens". Such mixed esters can be prepared by first acylating a sugar at a 1:1 mole ratio With a hydrocarbyl acid halide followed by reaction with the corresponding polyoxyalkylene acid halide or alkylene oxide to provide the desired material. The simple polyoxyalkylene ester of di-saccharides, especially sucrose, wherein the polyoxyalkylene groups contain up to about 20 alkylene oxide moieties are another useful class of sugar esters herein. A preferred sugar ester of this class is sorbitol trioleate ethoxylated with 20 moles of ethylene oxide. Mixtures of sugar esters with other polyol esters, eg. glcerol esters, are also suitable for use herein, for example, Palm Oil Sucroglyceride (Rhone-Poulenc).

As used herein, the term "lecithin" refers to a material which is a phosphatide. Naturally occurring or synthetic phosphatides can be used. Phosphatidylcholine or lecithin is a glycerine esterified with a choline ester of phosphoric acid and two fatty acids, usually a long chain saturated or unsaturated fatty acid having 16–20 carbons and up to 4 double bonds. Other phosphatides capable of forming lamellar or hexagonal liquid crystals can be used in place of the lecithin or in combination with it. These phosphatides are glycerol esters with two fatty acids as in the lecithin, but the choline is replaced by ethanolamine (a cephalin), or serine ( -aminopropanoic acid; phosphatidyl serine) or an inositol (phosphatidyl inositol). While the invention herein is exemplified with lecithin, it is understood that these other phosphatides can be used herein.

A variety of lecithins can be used. American Lecithin Company supplies a Nattermann Phospholipid, Phospholipan 80 and Phosal 75. Other lecithins which can be used alone or in combination with these are: Actifla Series, Centrocap series, Central Ca, Centrol series, Centrolene, Centrolex, Centromix, Centrophase and Centrolphil Series from Central Soya; Alcolec and Alcolec 439-C from American Lecithin; Canaspersa from Canada Packers, Lexin K and Natipide from American Lecithin; and L-Clearate, Clearate LV and Clearate WD from the W. A. Cleary Co. Lecithins are supplied dissolved in ethanol, fatty acids, triglycerides and other solvents. They are usually mixtures of lecithins and range from 15% to 50% of the solution as supplied.

Both natural and synthetic lecithins can be used. Natural lecithins are derived from oilseeds such as sunflower seeds, soybeans, safflower seeds and cottonseed. The lecithins are separated from the oil during the refining process.

The organic amphiphilic compound has been found to be especially valuable herein for improving the spreadability of make-up compositions which include substantial levels of humectant, especially glycerine, which can have an adverse effect on application characteristics and which can lead to tack and skin feel negatives.

According to a second aspect of the invention therefore, there is provided a make-up composition in the form of a gel or emulsion comprising:

a) from about 0.1% to about 30% by weight of humectant,
b) from about 0% to about 25% by weight of pigment,
c) from about 0.1% to about 20% by weight of an organic amphiphilic material which is capable of forming smectic lyotropic liquid crystals in product or on the skin, and
d) water.

In highly preferred compositions of this kind, the humectant (especially glycerine or another $C_2$–$C_6$ polyol) is present at a level of from about 10% to about 20% by weight. Gel-form compositions also preferably contain from about 0.01% to about 10% of a hydrophilic gelling agent.

Another desirable component herein is a pigment. Suitable pigments for use herein can be inorganic and/or organic. Also included within the term pigment are materials having a low colour or lustre such as matte finishing agents, and also light scattering agents. Examples of suitable pigments are iron oxides, acylglutamate iron oxides, ultramarine blue, D&C dyes, carmine, and mixtures thereof. Depending upon the type of make-up composition, whether foundation or blusher, a mixture of pigments will normally be used.

The foundation composition can also include at least one matte finishing agent. The function of the matte finishing agent is to hide skin defects and reduce shine. Such cosmetically acceptable inorganic agents, i.e., those included in the CTFA Cosmetic Ingredient Dictionary, Third Ed., as silica, hydrated silica, silicone-treated silica beads, mica, talc, polyethylene, titanium dioxide, bentonite, hectorite, kaolin, chalk, diatomaceous earth, attapulgite and the like may be utilized. Of particular usefulness as a matte finishing agent is low lustre pigment such as titanated mica (mica coated with titanium dioxide) coated with barium sulfate. Of the inorganic components useful as a matte finishing agent low lustre pigment, talc, polyethylene, hydrated silica, kaolin, titanium dioxide and mixtures thereof are particularly preferred. Materials suitable for use herein as light-scattering agents can be generally described as spherical shaped inorganic materials having a particle size of up to about 100 microns, preferably from about 5 to about 50 microns, for example spherical silica particles.

The total concentration of the pigment may be from about 0.1 to about 25% by weight and is preferably from about 1 to about 10% by weight of the total composition, the exact concentration being dependent to some extent upon the specific mixture of pigments selected for use in a foundation make-up or blusher to achieve the desired shades. The preferred compositions contain from about 2% to about 20% by weight of titanium dioxide and most preferably from about 5% to about 10% by weight of titanium dioxide.

The preferred pigments for use herein from the viewpoint of moisturisation, skin feel, skin appearance and emulsion compatibility are treated pigments. The pigments can be treated with compounds such as amino acids, silicones, lecithin and ester oils. The more preferred pigments are the silicone (polysiloxane) treated pigments.

The balance of the composition of the present invention is deionized water. The composition preferably comprises from about 30% to about 95%, more preferably from about 40% to about 80% by weight of the oil phase, and from about 5% to about 70%, more preferably from about 20% to about 60% by weight of the water phase.

The make-up compositions of the present invention can also comprise a particulate cross-linked hydrophobic acrylate or methacrylate copolymer. This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area (N2-BET) in the range from about 50 to 500, preferably 100 to 300m$^2$/g and having the active ingredient absorbed therein.

The cross-linked hydrophobic polymer when used herein is in an amount of from about 0.1% to about 10% by weight and is preferably incorporated in the external silicone-containing oil phase. The active ingredient can be one or more or a mixture of skin compatible oils, skin compatible humectants, emollients, moisturizing agents and sunscreens. The polymer material is in the form of a powder, the powder being a combined system of particles. The system of powder particles forms a lattice which includes unit particles of less than about one micron in average diameter, agglomerates of fused unit particles of sized in the range of about 20 to 100 microns in average diameter and aggregates of clusters of fused agglomerates of sizes in the range of about 200 to 1,200 microns in average diameter.

The powder material of the present invention which can be employed as the carrier for the active ingredient can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. The polymer has the structural formula:

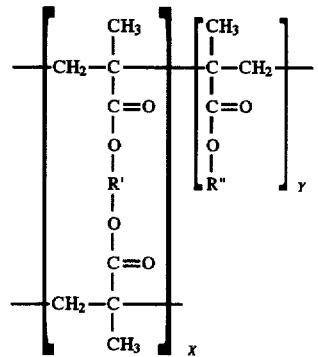

where the ratio of x to y is 80:20, R' is —$CH_2CH_2$— and R" is —$(CH_2)_{11}CH_3$.

The hydrophobic polymer is a highly crosslinked polymer, more particularly a highly cross-linked polymethacrylate copolymer. The material is manufactured by the Dow Corning Corporation, Midland, Michigan, USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersions or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant: carrier is from about 1:4 to about 3:1.

Also suitable as a highly cross-linked polymethacrylate copolymer is Microsponges 5647. This takes the form of generally spherical particles of cross-linked hydrophobic polymer having a pore size of from about 0.01 to about 0.05 µm and a surface area of 200–300m$^2$/g. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylpyrrolidone, polyvinylalcohol, polyquaternium-10, guar gum, hydroxypropyl guar gum and xanthan gum.

Among suitable hydrophilic gelling agents are acrylic acid/ethyl acrylate copolymers and the carboxyvinyl polymers sold by the B. F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10–30 Alkyl Acrylate Crosspolymer). A combination of the polyalkenyl polyether cross-linked acrylic acid polymer and the hydrophobically modified cross-linked acrylic acid polymer is also suitable for use herein. Other suitable gelling agents suitable for use herein are oleogels such as trihydroxystearin and aluminium magnesium hydroxy stearate. The gelling agents herein are particularly valuable for providing excellent stability Characteristics over both normal and elevated temperatures.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

The make-up compositions herein can additionally comprise an emollient. Emollients suitable for the compositions of the present invention include natural and synthetic oils selected from mineral, vegetable, and animal oils, fats and waxes, fatty acid esters, fatty alcohols, alkylene glycol and polyalkylene glycol ethers and esters, fatty acids and mixtures thereof.

Suitable emollients for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988,255, Seiden, issued Oct. 26 1976), lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyldimerate and triisostearyltrimerate.

Preferred emollients are selected from cetearyl isononanoate, isopropyl palmitate, isopropyl isostearate, cetyl octanoate, cetyl acetate, trioctyl titrate, PEG isoceteth-3 acetate, dioctyl maleate, propylene glycol dicaprylate/dicaprate, caprylic/caprio triglyceride, mineral oil, PPG-20 methylglucose ether, and lanolin alcohol, and mixtures thereof. These emollients may be used independently or in mixtures and may be present in the composition of the present invention in an amount from about 1% to about 30% by weight, and preferably are present in an amount from about 5% to about 15% by weight of the total composition.

The composition may also contain additional materials such as, for example, fragrances, fillers such as nylon, sun-screens, preservatives, proteins, antioxidants, chelating agents and water-in-oil emulsifiers as appropriate.

Another optional component of the make-up composition is one or more ultraviolet absorbing agents. Ultraviolet absorbing agents, often described as sunscreening agents, can be present in a concentration in the range of between about 1% and about 12% by weight, based on the total weight of composition. Preferably, the UV absorbing agents constitute between about 2% and 8% by weight. More preferably, the UV absorbing agents can be present in the composition in a concentration range of between about 4% and about 6% by weight. Of the ultraviolet absorbing agents suitable for use herein, benzophenone-3, octyl dimethyl PABA (Padimate O) and mixtures thereof are particularly preferred.

A chelating agent can also be incorporated in the make-up composition. A chelating agent is preferably present in the composition in a concentration in the range of between about 0.02% to about 0.10% by weight, based on the total weight of the composition. Preferably, the chelating agent is present in a concentration in the range of between about 0.03% and about 0.07% by weight, based on the total weight of the composition. Among the chelating agents that may be included in the composition is trisodium EDTA.

Another optional but preferred component of the foundation composition is one or more preservatives. The preservative concentration in the foundation composition, based on the total weight of that composition, is in the range of between about 0.2% and about 0.8% by weight, preferably between about 0.4% and about 0.6% by weight. Suitable preservatives for use herein include diazolidinyl urea, methyl paraben and ethyl paraben, and mixtures thereof.

The make-up compositions of the present invention can be in the form of foundations, blushers, concealers, compact powders, and the like, preferably as foundations and blushers.

The following Table is provided to illustrate compositions of the make-up of the present invention:

| Example | I Wt % | II Wt % | III Wt % | IV Wt % | V Wt % | VI Wt % | VII Wt % |
|---|---|---|---|---|---|---|---|
| A. | | | | | | | |
| Cetyloctanoate | 2.00 | 0.0 | 0.0 | 2.0 | 5.0 | 2.0 | 2.0 |
| Cyclomethicone | 8.574 | 12.25 | 12.25 | 15.0 | 12.0 | 8.574 | 8.57 |
| Cyclomethicone/dimethicone copolyol (90:10) | 17.16 | 20.0 | 20.0 | 5.0 | 8.0 | 10.0 | 17.16 |
| Propylparaben (33%) in laureth-7 | 0.75 | 0.75 | 0.75 | 0.75 | 0.75 | 0.75 | 0.75 |
| Dioctyl maleate | 0.0 | 0.0 | 0.0 | 0.0 | 10.0 | 0.0 | 0.0 |
| Dimethicone | 0.0 | 0.0 | 0.0 | 3.0 | 5.0 | 10.0 | 0.0 |
| Benzophenene-3 | 0.0 | 0.0 | 0.0 | 0.0 | 0.0 | 2.0 | 0.0 |
| Propylene glycol Dicaprylate/Dicaprate | 0.0 | 0.0 | 0.0 | 5.0 | 0.0 | 10.0 | 0.0 |
| B. | | | | | | | |
| Titanium Dioxide | 8.25 | 6.0 | 1.5 | 6.0 | 8.0 | 20.0 | 8.25 |
| Titanium Dioxide treated (Aluminium hydrate, stearic acid) | 0.25 | 0.5 | 3.0 | 0.25 | 0.25 | 0.0 | 0.25 |
| Titanated Micas | 0.1 | 0.1 | 0.1 | 0.25 | 1.0 | 0.0 | 0.1 |
| Talc | 3.387 | 4.5 | 6.0 | 0.7 | 0.7 | 0.7 | 3.387 |
| Silica | 0.6 | 4.25 | 6.0 | 4.25 | 0.6 | 0.6 | 0.6 |
| Nylon | 0.0 | 0.0 | 0.0 | 0.0 | 0.5 | 0.0 | 0.0 |
| C. | | | | | | | |
| Cyclomethicone/dimethicone copolyol (90:10) | 1.858 | 1.5 | 1.85 | 5.0 | 1.0 | 1.0 | 1.858 |
| Acrylates Copolymer | 0.0 | 1.0 | 0.0 | 0.0 | 0.0 | 0.0 | 0.0 |
| Acrylates Copolymer (loaded with glycerine) | 1.0 | 0.0 | 6.0 | 1.0 | 1.0 | 1.0 | 1.0 |
| D. | | | | | | | |
| Yellow Iron Oxide | 1.2 | 1.2 | 0.6 | 0.4 | 1.2 | 1.2 | 1.2 |
| Red Iron Oxide | 0.49 | 0.6 | 0.6 | 0.49 | 0.49 | 0.2 | 0.6 |
| Black Iron Oxide | 0.16 | 0.1 | 0.24 | 0.1 | 0.1 | 0.24 | 0.24 |
| Ultramarine Blue | 0.0 | 0.00 | 0.00 | 0.1 | 0.0 | 0.0 | 0.0 |
| Cyclomethicone | 0.0 | 0.0 | 0.0 | 0.0 | 0.68 | 0.0 | 0.0 |
| E. | | | | | | | |
| Synthetic Wax | 0.1 | 0.5 | 0.5 | 0.1 | — | — | — |
| Arachidyl behenate | 0.3 | — | — | 0.3 | 0.5 | 0.3 | 0.3 |
| Stearic Acid | 0.0 | — | — | — | — | — | 2.5 |
| Palmitic Acid | 0.0 | — | — | — | — | 2.5 | — |
| Silica (spheron P1500) | 6.0 | — | 6.0 | — | — | — | — |
| F. | | | | | | | |
| Trihydroxy-stearin | 0.3 | 0.3 | 1.5 | 1.5 | — | — | — |
| Cyclomethicone | 1.0 | 4.0 | — | — | 4.0 | 4.0 | 4.0 |
| Beeswax | 1.5 | 1.2 | — | — | 1.3 | — | — |
| Abil WED9 | — | 3.0 | — | — | — | — | — |
| Palm Oil Sucroglyceride | — | — | — | — | 4 | — | — |
| Sucrose Monooleate | 4 | 4 | 5 | 3 | — | 10 | 6 |
| G. | | | | | | | |
| Ethylene brassylate | 0.05 | 0.05 | 0.05 | 0.05 | 0.05 | 0.05 | 0.05 |
| BHT | 0.05 | 0.05 | 0.05 | 0.05 | 0.05 | 0.05 | 0.05 |
| H. | | | | | | | |
| Deionized water | | | | to 100 | | | |
| Methyl paraben (2.1%) in propylene glycol | 5.75 | 5.75 | 5.75 | 5.75 | 5.75 | 5.75 | 5.75 |
| Propylene glycol | 2.37 | 2.37 | 2.37 | 2.37 | 0.0 | 2.37 | 0.0 |
| Sodium chloride | 2.0 | 2.0 | 2.0 | 2.0 | 2.0 | 2.0 | 2.5 |
| Sodium dihydroacetate | 0.3 | 0.3 | 0.3 | 0.8 | 0.8 | 0.3 | 0.8 |
| Glycerine | 4.5 | 10.0 | 10.0 | 5.0 | 0.0 | 10.0 | 15.0 |
| Trisodium EDTA | 0.0 | 0.0 | 0.0 | 0.0 | 0.0 | 0.0 | 0.01 |
| Triethanolamine | 0.0 | 0.0 | 0.0 | 0.0 | 0.0 | 0.0 | 0.75 |
| Allantoin hydroxyethyl-cellulose | 0.0 | 0.0 | 0.1 | 0.0 | 0.0 | 0.0 | 0.0 |
| sunscreen | 0.0 | 0.0 | 0.1 | 0.0 | 0.0 | 0.0 | 0.0 |
| I. | 0.0 | 0.0 | 0.0 | 0.2 | 0.2 | 0.0 | 0.0 |
| Deionized Water | 0.0 | 0.0 | 0.0 | 0.0 | 10.0 | — | — |
| J. | | | | | | | |
| Propylene Glycol | 0.0 | 0.0 | 0.0 | 2.0 | 0.0 | 0.0 | 0.0 |
| Xanthan Gum | 0.0 | 0.0 | 0.0 | 0.08 | 0.0 | 0.0 | 0.0 |
| K. | | | | | | | |
| Essential Oils | 0.0 | — | — | 0.20 | — | — | — |
| Perfume Oil | 0.0 | 0.25 | — | 0.20 | — | — | — |
| Vitamin A Palmitate | 0.0 | 0.05 | — | — | — | — | — |
| L. | | | | | | | |
| Aloe Vera Gel | 0.0 | 0.0 | 3.0 | — | — | — | — |
| Chamomile Extract | 0.0 | 0.0 | 0.1 | — | — | — | — |

*Contains about 1% propylene glycol.

The various components listed in the Table have been segregated into groups, the constituents of each group being mixed together before being added to members of the remaining groups in accordance with the procedures set forth below.

In the first step, the mixture of components of phase A is stirred for approximately 5 minutes with sheer mixing until homogeneous. With high speed sheer mixing, the materials of phase B are added gradually to A and the batch is mixed for 20 minutes until dispersed.

The components of phase C and then phase D are slowly added to the mixture of phases A and B with high shear mixing until dispersed. Silica is added at this point and dispersed through the mixture.

The resulting batch heated to 90° C. before the addition of the components of phase E. The vessel is cooled to 55° C. and the premixed phase F is added. The batch is mixed until homogeneous. The mixture is cooled to 30° C. and phase G is added.

A premix of phase H is made by mixing all the components until completely dissolved. At 30° C. the premix of phase H is added to the batch mixture with high shear, ensuring that there is no excess water on the surface. The mixture is then milled for 15 minutes.

Finally phases I, J, K, and L are added as diluent.

The resulting make-up composition is ready for packaging.

The make-up compositions of the Examples exhibit improved moisturisation, spreadability, product stability and skin-feel benefits, with reduced shine and tackiness and improved skin appearance.

We claim:

1. A make up composition in the form of an oil-in-water emulsion comprising:
   a) from about 1% to about 50% by weight of silicone oil selected from volatile silicones, non-volatile silicones and mixtures thereof,
   b) from about 0.1% to about 30% by weight of humectant,
   c) from about 0.1% to about 25% by weight of pigment, and
   d) from about 0.1% to about 20% by weight of an organic amphiphilic material which is capable of forming smectic lyotropic liquid crystals containing said humectant in product or on the skin.

2. A make-up composition according to claim 1 wherein the amphiphilic material is selected from polyol esters, alkoxylated polyol esters and mixtures thereof.

3. A make-up composition according to claim 2 wherein the organic amphiphilic material comprises a sugar ester.

4. A make-up composition according to claim 1 wherein the volatile silicone oil is selected from cyclic polyorganosiloxanes having viscosities of less than about 10 centistokes and linear polyorganosiloxanes having viscosities of less than about 5 centistokes at 25 ° C., and mixtures thereof.

5. A make-up composition according to claim 4 wherein the volatile silicone oil is selected from cyclic polydimethylsiloxanes containing from about 3 to about 9 silicon atoms.

6. A make-up composition according to claim 1 wherein the non-volatile silicone oil comprises a polydiorganosiloxane-polyoxyalkylene copolymer containing at least one polydiorganosiloxane segment and at least one polyoxyalkylene segment.

7. A make-up composition according to claim 6 wherein the polydiorganosiloxane-polyoxyalkylene copolymer is dimethicone copolyol.

8. A make-up composition according to claim 1 wherein the humectant is selected from glycerine and polyglycerylmethacrylate lubricants having a viscosity of from about 300,000–1,100,000cps at 25° C., and mixtures thereof.

9. A make-up composition according to claim 8 wherein the humectant is glycerine.

10. A make-up composition according to claim 1 comprising from about 0.1% to about 10% by weight of the liquid crystal-forming organic amphiphilic material.

11. A make-up composition according to claim 1 wherein the silicone oil comprises from about 2% to about 25% by weight of composition of non-volatile silicones.

12. A make-up composition according to any of claim 1 wherein the pigment is silicone treated.

13. A make-up composition according to claim 1 comprising from about 5% to about 25% by weight of composition of humectant.

14. A make-up composition according to any of claim 1 additionally comprising from about 0.1% to about 10% by weight of a cross-linked hydrophobic acrylate or methacrylate copolymer.

15. A make-up composition according to claim 14 wherein the cross-linked hydrophobia copolymer is in the form of a lattice and wherein at least one active ingredient is dispersed uniformly throughout and entrapped within the copolymer lattice, the active ingredient being selected from skin compatible oils, skin compatible humectants, emollients, moisturizing agents and sunscreens.

16. A make-up composition according to claim 15 wherein the active ingredient is a humectant.

17. A make-up composition according to any of claim 1 additionally comprising from about 0.1% to about 10% by weight of a matte finishing agent selected from silica, hydrated silica, mica, talc, polyethylene, titanium dioxide, bentonite, hectorite, kaolin, chalk, diatomaceous earth and attapulgite, and mixtures thereof.

18. A make-up composition according to claim 17 wherein the matte finishing agent is selected from silica or hydrated silica.

19. A make-up composition according to any of claim 1 additionally comprising from about 1% to about 15% by weight of an emollient which is a natural or synthetic oil selected from mineral, vegetable and animal oils, fats and waxes, fatty acid esters, fatty alcohols, alkylene glycol and polyalkylene glycol ethers and esters, fatty acids and mixtures thereof.

20. A make-up composition according to claim 19 wherein the emollient is selected from isopropyl palmitate, isopropyl isostearate, dioctyl maleate, propylene glycol dicaprylate/propylene glycol dicaprate, caprylic triglyceride/capric triglyceride, squalane, mineral oil, cetearyl isononanoate and lanolin alcohol, and mixtures thereof.

21. A make-up composition according to any of claim 20 wherein the oil phase comprises form about 0.1% to about 10% by weight of humectant on a composition basis.

22. A make-up composition according to any of claim 21 comprising from by weight of the oil phase, and from about 5% to about 70%. by weight of the water phase.

23. A make-up composition according to claim 1 additionally comprising one or more ultraviolet absorbing agents.

24. A make-up composition in the form of a gel or emulsion comprising:
   a) from about 0.1% to about 30% by weight of humectant,
   b) from about 0% to about 25% by weight of pigment,
   c) from about 0.1% to about 20% by weight of an organic amphiphilic material which is capable of forming smectic lyotropic liquid crystals, containing said humectant, in product or on the skin, and
   d) water.

25. A make-up composition according to claim 24 comprising from about 10% to about 20% by weight of humectant.

* * * * *

UNITED STATES PATENT AND TRADEMARK OFFICE
CERTIFICATE OF CORRECTION

PATENT NO. : 5,688,831
DATED : November 18, 1997
INVENTOR(S) : Magda EL-Nokaly, et. al.

It is certified that error appears in the above-identified patent and that said Letters Patent is hereby corrected as shown below:

Column 4, line 39 "tool" should read --mol--.

Column 5, line 9 "CRTM)" should read --(RTM)--.

Column 6, line 53 "laurie" should read --lauric--.

Column 7, line 7 "$R_1$" should read --$R^1$--.

Column 15, line 4 "Mother" should read --Another--.

Signed and Sealed this

Seventh Day of April, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,688,831

DATED : November 18, 1997

INVENTOR(S) : MAGDA EL-NOKALY

It is certified that error appears in the above-identified patent and that said Letters Patent is hereby corrected as shown below:

Column 17, line 14 "oil-in-water" should read --water-in-oil--.

Signed and Sealed this

Eighth Day of June, 1999

Q. TODD DICKINSON

*Attest:*

*Attesting Officer*     Acting Commissioner of Patents and Trademarks